United States Patent [19]

Kohsai et al.

[11] Patent Number: 5,447,152
[45] Date of Patent: Sep. 5, 1995

[54] ENDOTRACHEAL TUBE AND THE METHOD OF MANUFACTURING IT

[75] Inventors: Tadashi Kohsai; Nobuaki Mihara, both of Fujinomiya, Japan

[73] Assignee: Terumo Kabushiki Kaisha, Tokyo, Japan

[21] Appl. No.: 930,716

[22] Filed: Aug. 14, 1992

[51] Int. Cl.⁶ .......................................... A61M 16/00
[52] U.S. Cl. ........................... 128/207.15; 128/207.14
[58] Field of Search ....................... 128/207.14, 207.15

[56] References Cited

U.S. PATENT DOCUMENTS

| | | | |
|---|---|---|---|
| 3,854,484 | 12/1974 | Jackson | 128/207.15 |
| 3,865,666 | 2/1975 | Shoney | 604/103 |
| 4,055,682 | 10/1977 | Merrill | 604/103 |
| 4,130,617 | 12/1978 | Wallace | 264/528 |
| 4,251,305 | 2/1981 | Becker et al. | 156/86 |
| 4,331,142 | 5/1982 | Degen | 128/207.15 |
| 4,387,711 | 6/1983 | Merry | 128/207.15 |
| 4,411,055 | 10/1983 | Simpson et al. | 29/447 |
| 4,453,940 | 6/1984 | Aoyagi et al. | 604/408 |
| 4,511,354 | 4/1985 | Sterling | 128/207.15 |
| 4,611,018 | 9/1986 | Derencsenyi | 524/130 |
| 4,841,007 | 6/1989 | Zdrahala et al. | 528/28 |

FOREIGN PATENT DOCUMENTS

| | | |
|---|---|---|
| 1449782 | 8/1966 | France . |
| 63-77050 | 5/1988 | Japan . |
| 61-154678 | 8/1988 | Japan . |
| 63-206254 | 8/1988 | Japan . |
| 4-102461 | 4/1992 | Japan . |

OTHER PUBLICATIONS

Patent Abstracts of Japan, vol. 16, No. 342 (C-0966), 24 Jul. 1992 of JP-A-41 02 461 (Terumo Corp.), 3 Apr., 1992.
Patent Abstracts of Japan, vol. 16, No. 400 (C-977), 25 Aug. 1992 of JP-A-41 32 563 (Terumo Corp.), 6 May, 1992.
DATABASE WPI, AN 93-088001 (11), Derwent Publications Ltd., London, GB of JP-A-50 31 192 (Terumo), Feb. 9, 1993.

*Primary Examiner*—Edgar S. Burr
*Assistant Examiner*—Aaron J. Lewis
*Attorney, Agent, or Firm*—Frishauf, Holtz, Goodman, Langer & Chick

[57] ABSTRACT

An endotracheal tube comprising a tubular body having a lumen and an inflation lumen provided in parallel with the lumen, and an inflatable and deflatable cuff attached to the distal end portion of the tubular body so as to surround the outside surface of the tubular body and communicate with the inflation lumen, characterized by said cuff being made of a flexible fluoroplastic, a mixture of a flexible fluoroplastic and a thermoplastic resin or a partly cross-linked resin with a low laughing gas permeability.

7 Claims, 4 Drawing Sheets

ENDOTRACHEAL TUBE AND THE METHOD OF MANUFACTURING IT

FIELD OF THE INVENTION

The present invention relates to an endotracheal tube used for general anesthesia before surgery and post surgical artificial respiratory and also to the method of manufacturing the tube.

As shown in FIG. 4, an endotracheal tube 40 is inserted into the trachea 43 of a patient 42, and the cuff 45 at the distal end is inflated by the air injected through the pilot balloon 44 so as to fit tightly inside the trachea 43 making airtight between the tube and the trachea; and the proximal end of the tube is connected by means of the connector 46 and the corrugated tubes 48 to an anesthesia machine or an artificial respiratory apparatus (not shown in FIG. 4).

When administering laughing gas ($N_2O$) through such a tube into the body of a patient, the gas having a high permeating and diffusing power is at first rapidly absorbed into the patient's body to produce anesthesia. After having reached the saturation point in the body tissue, the laughing gas in the air around the cuff passes into the cuff 45 formed of flexible thin film of vinyl chloride. Because of its permeating power greater than that of air. The laughing gas thus permeating into the cuff causes a rise in the internal pressure of the cuff.

It was reported that the cuff fitted tightly inside the trachea to secure the endotracheal tube to the trachea airtight caused various damages to the trachea as the internal pressure of the cuff increases; specifically fracturing the cartilage of the trachea and hindering the formation of the mucous membrane protecting the inside surface of the trachea. Particularly the hindrance of the formation of the mucous membrane can cause serious damages to the trachea and the vocal cords.

Endotracheal tubes to solve the above problem are disclosed by Japanese Patent Provisional Publication gazette No. 154678/86 and No. 263455/86. Although the laughing gas permeability of these endotracheal tubes is considerably low, a still lower laughing gas permeability is needed in recent years.

Conventional cuffs are made by forming a tube out of a synthetic resin and blow-molding the tube into a cuff. Therefore, a blow-moldable resin must be used for the material for the conventional cuffs. Resins not blow-moldable (those which break when drawn by blow-molding, for example) cannot be used if the resin has a low laughing gas permeability. Further, those blow-moldable but the strength (particularly withstanding pressure when inflated) of the cuff formed of which is not sufficient also cannot be used. Thus a resin blow-moldable and having physical property required for the cuff must be used out of necessity if its laughing gas permeability is rather high. For this reason the laughing gas permeability of conventional endotracheal tubes is not low enough.

SUMMARY OF THE INVENTION

The first object of present invention is to provide an endotracheal tube which can substantially prevent the permeation of laughing gas.

The second object of present invention is to provide a method of manufacturing an endotracheal tube the cuff of which can be formed of a resin with a very low laughing gas permeability by blow-molding.

The first object is attained by the first endotracheal tube of the present invention comprising a tubular body having a lumen and an inflation lumen provided in parallel with the lumen, and an inflatable and deflatable cuff attached to the distal end portion of the tubular body so as to surround the outside surface of the tubular body and communicate with said cuff, characterized by the cuff being made of a flexible fluoroplastic or a mixture of a flexible fluoroplastic and a thermoplastic resin.

The first object is also attained by the second endotracheal tube of the present invention comprising a tubular body having a lumen and an inflation lumen provided in parallel with the lumen, and an inflatable and deflatable cuff attached to the distal end portion of the tubular body so as to surround the outside surface of the tubular body and communicate with said cuff, characterized by the cuff being made of a partly cross-linked resin with a low laughing gas permeability.

The second object is attained by the method of the present invention of manufacturing an endotracheal tube comprising the processes of forming the tubular body, forming the cuff, and attaching the cuff to the tubular body, characterized by the process of forming the cuff comprising the process of forming a tube of a resin with a low laughing gas permeability, the process of irradiating the tube with electron beams or X rays to form cross-links partly in the resin, and the process of blow-molding the tube into the cuff.

DETAILED DESCRIPTION OF THE PREFERRED EMBODIMENTS

The endotracheal tube of the present invention is described below in detail with reference to the drawings.

Figure 1:
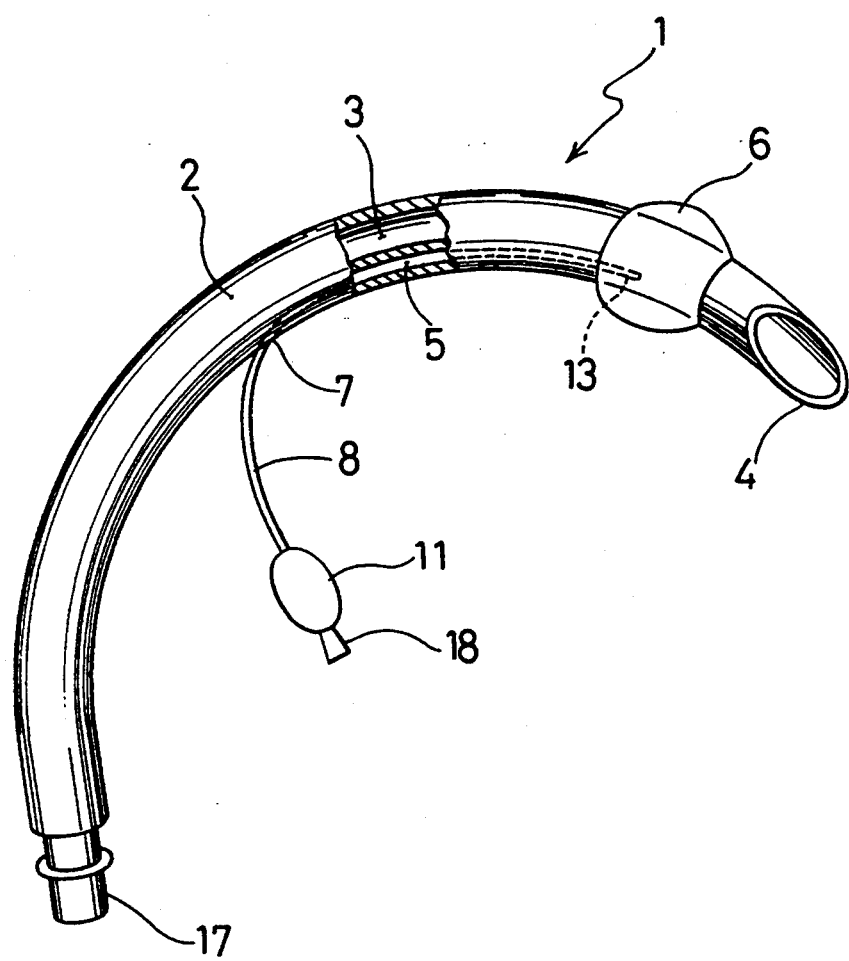
FIG. 1 is a part-sectional diagrammatic view of an embodiment of the endotracheal tube of the present invention.
Figure 2:
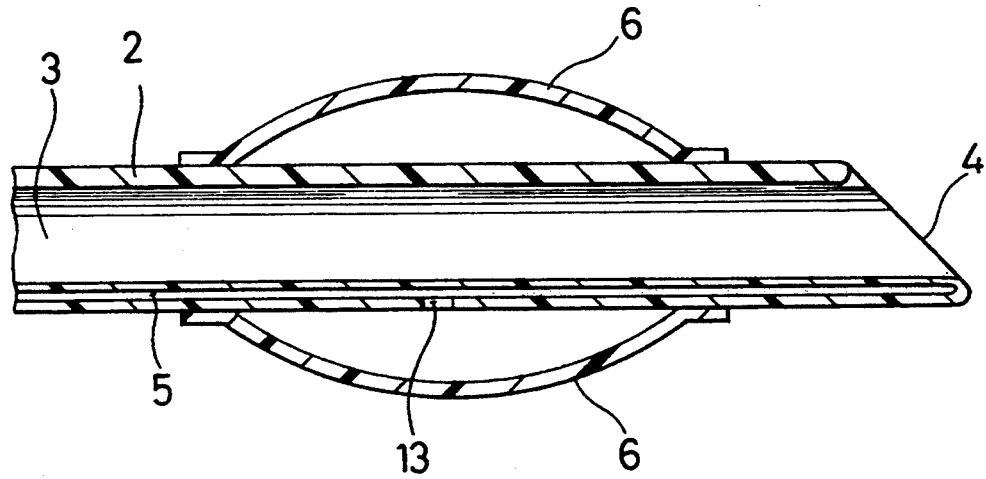
FIG. 2 is an enlarged sectional view of the distal end portion of the endotracheal tube shown in FIG. 1.
Figure 3:
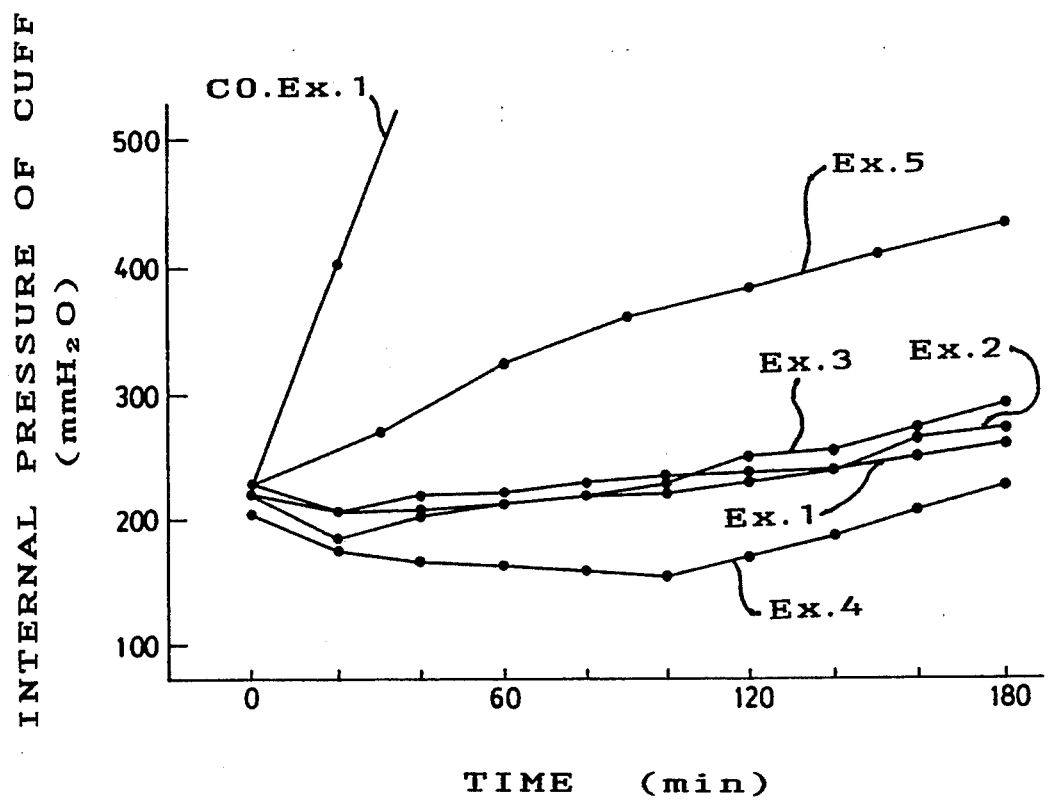
FIG. 3 shows the results of the tests conducted using the endotracheal tubes of the examples of the present invention and those of comparative examples.
Figure 4:
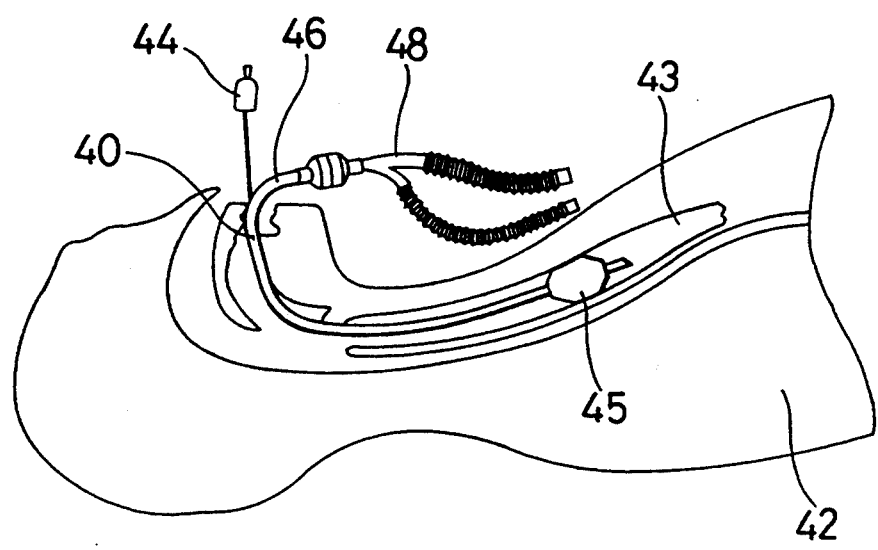
FIG. 4 shows an endotracheal tube put in the trachea for use.

As shown in FIGS. 1 and 2, the endotracheal tube of the present invention 1 comprises a tubular body 2 having a lumen 3 inside it and an inflation lumen 5 provided along the lumen 3, and an inflatable and deflatable cuff 6 attached to the distal end portion of the tubular body 2 so as to surround the outside surface of the tubular body 2 and communicate with the inflation lumen 5.

The cuff 6 is formed of a flexible fluoroplastic or a mixture of a flexible fluoroplastic and a thermoplastic resin.

The tubular body 2 is made of a flexible synthetic resin and has a lumen 3 for introducing an anesthetic gas, oxygen and other gases formed from the distal end to the proximal end. The distal end 4 of the tubular body 2 is shaped to a smooth bevel as shown in FIG. 2 to facilitate the insertion of the tube into the body. Attached to the proximal end of the tubular body 2 is a connector 17 for connecting the tubular body 2 to a gas supplying apparatus. For the resin for the tubular body 2, soft vinyl chloride, polyurethane and silicone rubber, for example, are preferably usable.

The inflation lumen 5, smaller in diameter than the lumen 3, is formed in the wall of the tubular body 2 in parallel with the lumen 3 as shown in FIG. 2. The inflation lumen 5 is closed near the beveled end 4 and communicates with the inside space of the cuff 6 through the opening 13 formed in the outside surface of the wall of the tubular body 2 as shown in FIG. 2. An inflation tube 8 is connected to the inflation lumen 5 through an opening 7 formed in the outside surface of the wall near the proximal end of the tubular body 2 as shown in FIG. 1.

The inflation tube 8 may be connected to the inflation lumen 5 by inserting a heated mandrel into the inflation lumen 5 and pulling it out, then immediately inserting an end of the inflation tube 8 into the inflation lumen 5 or by bonding an end of the inflation tube 8 to the inflation lumen 5 of tubular body 2 by means of an adhesive.

The inflation tube 8 is provided near the rear end with a pilot balloon 11 for monitoring the degree of inflation of the cuff 6 and at the rear end with an adapter 17 in which a normally-closed check valve is housed (not shown). The adapter 17 is designed so that an instrument for injecting air to inflate the cuff 6 (syringe, for example) can be connected to it. The check valve in the adapter 17 opens when the inflation instrument is connected to the adapter.

Further, the tubular body 2 is preferably provided with a strip made of a material impervious to X rays along the axis through its overall length in order to allow monitoring the position of the tubular body 2, particularly its distal end.

The cuff 6 is attached to the distal end portion of the tubular body 2 so as to surround the tubular body. The cuff 6 is made of a soft fluororesin (flexible fluoroplastic) or a mixture of a soft fluororesin and a thermoplastic resin.

Flexible fluoroplastic is a resin which has the elasticity of fluororubber and the blow-moldability of fluororesin. Included in this type of resin are graft copolymer of a fluororubber and a crystalline fluororesin (fluororesin is grafted to the trunk consisting of a fluororubber) and block copolymer of fluororubber and crystalline fluororesin, for example.

More specifically, for the graft polymer of a fluororubber and a crystalline fluororesin, one in which a crystalline copolymer (side chain) containing at least one kind of fluorine-containing monomer is grafted to a fluorine-containing elastic copolymer (main chain) containing the peroxide group in the molecule and having the glass transition temperature below the room temperature is preferable.

The fluorine-containing elastic copolymer (trunk copolymer) making up the main chain contains the peroxide group of 0.02 to 0.2 wt % and is preferably composed using as the base the fluorine elastomer with the glass transition temperature (Tg) below the room temperature so that it have a sufficient elasticity. Particularly to obtain a high elasticity, it is preferable to select the constituents and ratio appropriately. Many known kinds of fluorine elastomers, such as copolymer of vinylidene fluoride (VDF) and hexafluoropropylene (HFP), ternary copolymer of VDF, HFP and tetrafluoroethylene (TFE), copolymer of VDF and chlorotrifluoroethylene (CTFE), copolymer of TFE and polypropylene, copolymer of TFE and florine-containing vinyl ether, and copolymer of a hydrocarbon diene compound and a florine-containing monomer can be used.

For the crystalline polymer containing at least one kind of fluorine-containing monomer (crystalline fluororesin) making up the side chains, polytetrafluoroethylene, polychlorotrifluoroethylene, poly(vinylidene fluoride), poly(vinyl fluoride), copolymer of TFE and ethylene, copolymer of CTFE and ethylene and copolymer of TFE and florine-containing vinyl ether can be used.

The graft copolymer is produced, for example, by adding a reducing agent and further a metal ion to a base polymer latex containing the peroxide group and then adding a crystalline fluororesin to the base polymer latex at a low temperature of 20° to 50° C. to graft polymerize. For the reducing agent are sodium hydrogensulfite, sodium sulfite, sodium thiosulfate and sodium peroxodisulfate are usable. For the metal ions, the salt containing iron (II) ion, cobalt ion or copper ion, that is, ferrous chloride, cobalt chloride and copper chloride are usable. The amount of these reducing agents are determined according to the total amount of the unsaturated peroxide copolymerized with the base polymer prepared, and normally 0.5 to 10 times the amount of the base polymer is preferable.

For the block copolymer, those the elastomer segment of which is vinylidene fluoride/hexafluoropropylene or pentafluoropropylene/tetrafluoroethylene (15 to 90:5 to 50: 0 to 35 in molar ratio) polymer or of perfluoro (C1 to C3 alkyl vinyl ether)/tetrafluoroethylene/vinylidene fluoride (15 to 75: 0 to 85: 0 to 85 in molar ratio) polymer and the nonelastomer element of which is vinylidene fluoride/tetrafluoroethylene (0 to 100 : 0 to 100 in molar ratio) polymer, ethylene/tetrafluoroethylene/hexafluoropropylene (40 to 60: 60 to 40: 0 to 30 in molar ratio), or 3,3,3-trifluoropropylene-1,2-trifluoromethyl-3,3,3-trifluoropropylene-1 or perfluoro (C1 to C3 alkyl vinyl ether) (40 to 60: 60 to 40: 0 to 30 in molar ratio) are preferable.

For the thermoplastic resin to mix with fluororubber, polyurethane, nylon(polyamide), polyester, polypropylene, polyethylene, polyolefin elastomer, ethylenevinyl acetate copolymer (EVA), polystyrene, polybutadiene and a mixture of them can be used.

Since the present invention uses a flexible fluoroplastic or a mixture of a flexible fluoroplastic and a thermoplastic resin moldable by heating as described above, the cuff 6 of the present invention can be easily formed and has the characteristics suitable for the endotracheal tube.

The maximum microcirculation pressure (the blood pressure in the microvascular in the superficial layer of the mucous membrane of trachea with where the cuff is in contact) is normally 450 mmH$_2$O and the initial pressure of the cuff 6 is generally 200 mmH$_2$O. Accordingly the rise in the internal pressure of the cuff 6 in use caused by the laughing gas permeating the cuff 6 must be less than 250 mmH$_2$O. Made of the resin as described above, the cuff 6 of the present invention satisfies this requirement enough, that is, the rise in the internal pressure is below 250 mmH$_2$O in 180 minutes.

Further, the cuff 6 must be soft enough so that it can be easily inflated and deflated and does not hurt the mucous membrane of the trachea. Therefore, taking the softness into consideration, it is preferable that the resin used for the cuff 6 has the thickness of 0.03 to 0.3 mm and the Shore A hardness of 70 to 90.

The permeability to laughing gas of the material for the cuff 6 is preferably 2 cc(STP)·cm/cm$^2$·sec·cmHg $\times 10^{-10}$ or smaller and particularly 1.8 cc(STP)·cm/cm$^2$·sec·cmHg $\times 10^{-10}$ or smaller.

The cuff 6 formed as described above is attached to the tubular body 2 in an airtight fashion by means of an adhesive, a solvent, heat or ultrasonic waves so that the opening 13 communicating with the inflation lumen 5 is open in the inside space of the cuff 6.

The endotracheal tube 1 of another embodiment of the present invention comprises a tubular body 2 with a lumen 3 inside it, an inflatable and deflatable cuff 6 attached to the distal end portion of the tubular body 2 so as to surround the outside surface of the tubular body 2, and an inflation lumen 5 provided along the lumen 3 and communicating with the cuff 6.

The cuff 6 of this endotracheal tube 1 is made of a resin with a low laughing gas permeability subjected to a cross-linking process.

By this partial cross-linking, resins which has a low laughing gas permeability but is not usable for the cuff because of the heat resistance not enough to blow-mold or the insufficient drawing strength or withstanding pressure are changed to have the sufficient physical properties (strength and withstanding pressure) maintaining the low laughing gas permeability inherent in them.

The endotracheal tube of this embodiment is different from that of the embodiment described above in that the cuff 6 is made of a resin with a low laughing gas permeability subjected to a cross linking process, the other construction is the same.

For the resin with a low laughing gas permeability, a flexible fluoroplastic, a mixture of a flexible fluoroplastic and a thermoplastic resin, saponified ethylene-vinyl acetate, and a mixture of saponified ethylene-vinyl acetate and a thermoplastic resin are usable.

Flexible fluoroplastic and a mixture of a flexible fluoroplastic and a thermoplastic resin are preferable. For the flexible fluoroplastic and the mixture of a flexible fluoroplastic and a thermoplastic resin, those described above are preferable.

Partial cross-linking is to cause the formation of cross-links in resins leaving unlinked part. The degree of partial cross-linking is indicated by the gel fraction (the gel content), for example. The gel fraction of the partly cross-linked material is preferably 10 to 50% and particularly 15 to 45%. By thus partly cross-linked, the material is changed to have the physical properties (strength and withstanding pressure) required for the cuff, maintaining the weldability to the tubular body 2 by unlinked part left.

The gel fraction indicates the proportion of cross-linked parts (gelled parts) in a resin and is calculated by the following equation:

$$Gel\ Ratio(Gel\ Fraction) = W2/W1 \times 100\ (\%)$$

where W1 is the total weight of the resin and W2 is the weight of cross-linked parts (gelled parts).

The maximum microcirculation pressure (the microvascular pressure in the superficial layer of the mucous membrane of trachea with where the cuff is in contact) is normally 450 mmH$_2$O and the initial pressure of the cuff 6 is generally 200 mmH$_2$O. Accordingly the rise in the internal pressure of the cuff 6 in use caused by the laughing gas permeating the cuff 6 must be less than 250 mmH$_2$O. Made of the resin as described above, the cuff 6 of the present invention satisfies this requirement enough, that is, the rise in the internal pressure is below 250 mmH$_2$O in 180 minutes.

Further, the cuff 6 must be soft enough so as to be easily inflated and deflated without hurting the mucous membrane of the trachea and have the physical properties (strength and withstanding pressure) required for the cuff. Therefore, taking the softness into consideration, it is preferable that the resin used for the cuff 6 has 0.03 to 0.3 mm thickness, 90 or smaller Shore A hardness, and about 1500 mmH$_2$O or greater withstanding pressure. Further, the strength of the resin formed into the cuff is preferably equal to or greater than 3 kgf.

Next described is the method of manufacturing the endotracheal tube of the present invention.

The method of the present invention is a method of manufacturing an endotracheal tube comprising a tubular body 2 with a lumen 3 inside it, an inflatable and deflatable cuff 6 attached to the distal end portion of the tubular body 2 so as to surround the outside surface of the tubular body 2, and an inflation lumen 5 provided along the lumen 3 and communicating with the cuff 6, characterized by the process of forming the cuff 6 in which a tube is formed of a resin with a low laughing gas permeability, the tube is irradiated with electrons or X rays to cause cross-links to form, and the tube is formed into the cuff 6 by blow-molding.

More specifically, the manufacturing method of the present invention comprises the processes of forming the tubular body 2, forming the cuff 6, and attaching the cuff 6 to the tubular body 2.

The tubular body 2 is formed, for example, by extrusion-molding a resin described above into a tube with the lumen 3 extending throughout the length of the tube and the lumen 5 closed at the distal end as shown in FIG. 2, cutting the distal end of the tube to a bevel, and heating the beveled end 4 to round the edges.

The cuff 6 is formed by the following process. First, a tube is formed of a resin with a low laughing gas permeability. For the resin with a low laughing gas permeability, those described above are usable. The inside diameter of the tube is preferably about 5 to 12 mm and the outside diameter about 7 to 15 mm.

This tube is put in an apparatus for applying gamma rays or electron beams to cause cross-links to form. The degree of cross-linking is preferably 10 to 50% and particularly 15 to 45% in the gel fraction. The dose of irradiation is determined depending upon the kind of the resin and a desired degree of cross-linking. Generally, in the case of gamma rays irradiating the resin by 1 to 8 Mrad, preferably 2 to 4 Mrad.

The thus-formed partly cross-linked tube is put in a metal mold with the inside surface formed in the shape of the cuff fully inflated and one end of the tube is clamped in an airtight fashion. The clamp is made by heat or ultrasonic waves or by means of a forceps. The tube is then heated to soften by the heating means of the metal mold when the metal mold is provided with one (an electric heater, for example), otherwise by introducing hot air into the tube from the open end. The heated part of the tube is tightly pressed against the inside surface of the metal mold by the introduction of warm air when the tube is heated by the heating means of the metal mold or by the hot air when the tube is heated by hot air. The tube is then cooled by free cooling, taken out of the metal mold, and both end portions of the tube are cut off to obtain the cuff.

Next, a part of the outside surface of the tubular body 2 is cut away to connect the inflation tube 8 to the inflation lumen 5. The inflation tube 8 is connected to the lumen 5 by inserting a heated mandrel into the lumen 5, pulling it out, and immediately fitting an end of the inflation tube 8 into the lumen 5 or by bonding an end of the inflation tube by means of an adhesive, for example.

Then formed at the distal end portion of the tubular body 2 around where the cuff 6 is attached is an opening 13 to connect the lumen 5 with the outside. The cuff 6 is put on the tubular body 2 so that the opening 13 is open in the cuff 6 and attached to the tubular body 2 in an airtight fashion by means of an adhesive or by welding by heat or ultrasonic waves.

EXAMPLES

Examples of the present invention are described below.

Examples 1 to 3

Tubular bodies (inside diameter 8 mm, outside diameter 11 mm, wall thickness 1.5 mm, inflation lumen 0.3 mm in diameter formed in the wall) were formed by extrusion-molding soft vinyl chloride resin (containing 110 parts by weight of plasticizer DOP for 100 parts by weight of poly(vinyl chloride)).

The distal end of each tube was cut obliquely to the axis and put in a metal mold with a heating means to round the edges. Next formed near the distal end of the inflation was an opening for connecting the inflation lumen with the cuff. Further, an opening was formed at the proximal side of the inflation lumen. An inflation tube provided with a pilot balloon and an adapter with a check valve housed is inserted into the opening and bonded by means of an adhesive.

Next, tubes (outside diameter 5.6 mm, wall thickness 0.3 mm) were formed using a flexible fluoroplastic (CEFRAL SOFT G880R, Shore A hardness: 80, Central Glass Co.). Each tube was put in a metal mold with the inside surface formed in the shape of the cuff inflated to the full and one end of the tube was clamped. The tube was softened and pressed against the inside surface of the metal mold by hot air introduced from the other end and cooled by free cooling. Thus three cuffs were obtained. The wall thicknesses of the portions connected to the tubular body, the largest-diameter portion, and the portions near the ends of the inflating portion of these cuffs were measured and shown in Table 1.

Each cuff was put on each tubular body and both ends of the cuff were connected airtight to the tubular body by heat-welding to obtain the endotracheal tubes of the present invention (examples 1 to 3).

Example 4

The endotracheal tube of the present invention (example 4) was made by the same way as example 1 except that the cuff was formed of a mixture of a flexible fluoroplastic (CEFRAL SOFT, Shore A hardness: 80, Central Glass Co.) and ethylene-butadiene thermoplastic resin (TUCTEC, Asahi Chemical Industry Co.). The mixture has the Shore A hardness 76. The wall thicknesses of the portions connected to the tubular body, the largest-diameter portion, and the portions near the ends of the inflating portion of the cuff of this example were as shown in Table 1.

Example 5

The endotracheal tube of the present invention (example 5) was made by the same way as example 1 except that the cuff was formed of a flexible fluoroplastic (DAIEL THERMOPLASTIC T-530, Shore A hardness: 67, Daikin Industries Co.).

TABLE 1

| | Wall Thickness (mm) | | |
|---|---|---|---|
| | Portions connected to tube | Largest-diameter portion | Ends of inflating portion |
| Ex 1 | 0.391 | 0.064 | 0.265 |
| Ex 2 | 0.279 | 0.054 | 0.165 |
| Ex 3 | 0.360 | 0.065 | 0.224 |
| Ex 4 | 0.305 | 0.043 | 0.193 |
| Ex 5 | 0.325 | 0.070 | 0.190 |

Comparative Example 1

An endotracheal tube for comparison (comparative example 1) was made by the same way as example 1 except that the cuff was formed of vinyl chloride.

The wall thickness of the cuff was 0.3 mm at the end portions connected to the tubular body, 0.11 mm at the largest-diameter portion, and 0.15 mm near the ends of the inflating portion.

Tests

The following tests were conducted on the endotracheal tubes of examples 1 to 5 and comparative example 1.

Test 1

The internal pressure of the cuff of each endotracheal tube was measured 180 minutes after the endotracheal tubes of examples 1 to 5 and comparative example 1 were put in contact with laughing gas, and the rise in the internal pressure was calculated from the initial internal pressure of the cuff. The results are as shown in Table 2. The relationship between the length of time during which the endotracheal tubes were put in contact with laughing gas and the internal pressure of the cuffs are shown in Table 3.

TABLE 2

| | Internal Pressure of Cuff (max) (mmH$_2$O)[after 180 min] | Rise of Internal Pressure of Cuff (max) (mmH$_2$O)[after 180 min] |
|---|---|---|
| Ex 1 | 250 | 50 |
| Ex 2 | 270 | 70 |
| Ex 3 | 280 | 80 |
| Ex 4 | 210 | 10 |
| Ex 5 | 430 | 230 |
| Co. Ex. 1 | 470 (at 30 min) | 270 (at 30 min) |

Test 2

The flexible fluoroplastic (Sample 1) used in examples 1 to 3 and vinyl chloride (Sample 2) used in the comparative example 1 were formed into films and their laughing gas permeability was each measured twice. The results are shown in Table 3.

TABLE 3

| | | Laughing Gas Permeability | | |
|---|---|---|---|---|
| | Thickness | First | Second | Average |
| Sample 1 | 200 μm | 1.7 | 1.86 | 1.78 |
| Sample 2 | 150 μm | 58.2 | 56.7 | 57.5 |

The unit of the laughing gas permeability is cc(STP)-cm/cm$^2$·sec·cmHg $\times 10^{-10}$.

This test was conducted using a film gas permeability tester (K-315N, Rikaseiki Kogyo Co.) and laughing gas for the measuring gas by the pressure method (low-vacuum method) at the measuring temperature 23×C. under the gas pressure 760 mmHg.

Example 6

A tubular body (inside diameter 8 mm, outside diameter 11 mm, wall thickness 1.5 mm, inflation lumen 0.3 mm in diameter formed in the wall) was formed by extrusion-molding soft vinyl chloride resin (containing 110 parts by weight of plasticizer DOP for 100 parts by weight of poly(vinyl chloride)).

The distal end of each tubular body was cut obliquely to the axis and put in a metal mold with a heating means to round the edges. Next formed near the distal end of the inflation lumen was an opening for connecting the inflation lumen with the cuff. Further, an opening was formed at the proximal side of the inflation lumen, and an inflation tube provided with a pilot balloon and an adapter with a check valve housed in it is inserted into the opening and bonded airtight by means of an adhesive.

Next, a tube (outside diameter 5.6 mm, wall thickness 0.3 mm) was formed using a flexible fluoroplastic (CEFRAL SOFT G880R, Shore A hardness: 80, Central Glass Co.). The tube was irradiated with 4 Mrads of gamma rays in the air to cause partial cross-linking to form in the resin. The gel fraction of the partly cross-linked resin was 19.5%.

The measurement of the gel fraction was conducted by the following method. The partly cross-linked resin 1 g (W1) cut from the tube was put in ETFE mesh (AFLON CLOTH AF80, Diameter of fiber: 0.12 mm, mesh/inch: 80×80, Opening: 0.198 mm) and dipped in 30 ml DMF (dimethylformamide), a solvent which dissolves only the uncloss-linked portion of the resin, for more than 24 hours. The sample, together with the meshes, were pulled out from DMF and dipped in a fluorocarbon to leach out DMF into the fluorocarbon. After pulled out from the fluorocarbon, the sample was put in an oven at 80° C. for the night to dry. Then the weight (W2) the sample (cross-linked portion of the resin) was measured and the gel fraction was calculated by the above mentioned equation: W2/W1×100 (%), where W1 represents the total weight of the sample resin and W2 the weight of the cross-linked portion (gelled portion).

Next, the irradiated tube was put in a metal mold with the inside surface formed in the shape of the cuff inflated to the full, clamped airtight at one end, softened and inflated to press against the inside surface of the metal mold by the hot air (230° C.) introduced into it from the other end, and cooled. Both ends of the tube were cut off to obtain the cuff. The wall thickness of the cuff was 0.3 mm at both end portions connected to the tubular body, 0.05 mm at the largest-diameter portion, and 0.2 mm at both end portions of the inflating portion.

The cuff was put on the tubular body and both ends of the cuff were connected airtight to the tubular body by heat-welding. Thus made was the endotracheal tube of the present invention (example 6).

Example 7

The endotracheal tube of the present invention (example 7) was made by the same way as example 6 except that the tube for the cuff was irradiated with 2 Mrads of gamma rays in vacuum. The gel fraction of the irradiated resin was 29.7%. The wall thickness of the cuff was 0.3 mm at both end portions connected to the tubular body, 0.05 mm at the largest-diameter portion, and 0.2 mm at both end portions of the inflating portion.

Example 8

The endotracheal tube of the present invention (example 8) was made by the same way as example 6 except that the tube for the cuff was irradiated with 4 Mrads of gamma rays in vacuum. The gel fraction of the irradiated resin was 41.2%. The wall thickness of the cuff was 0.3 mm at both end portions connected to the tubular body, 0.05 mm at the largest-diameter portion, and 0.2 mm at both end portions of the inflating portion.

Example 9

The endotracheal tube of the present invention (example 9) was made by the same way as example 6 except that the tube for the cuff was formed of a mixture of a flexible fluoroplastic (CEFRAL SOFT, Shore A hardness: 80, Central Glass Co.) and styrene-ethylene-butadiene thermoplastic resin (TUFTEC, Asahi Chemical Industry) with the Shore A hardness 76 and that the partial cross-linking treatment was made by 4 Mrads of gamma rays in the air.

The wall thickness of the cuff was 0.3 mm at both end portions connected to the tubular body, 0.05 mm at the largest-diameter portion, and 0.2 mm at the end portions of the inflating portion.

Comparative Example 2

An endotracheal tube for comparison (comparative example 2) was made by the same way as example 6 except that the material of the cuff was vinyl chloride and that the material was not subjected to the partial cross-linking treatment.

The wall thickness of the cuff made of vinyl chloride was 0.3 mm at the end portions connected to the tubular body, 0.11 mm at the largest-diameter portion, and 0.15 mm at the end portions of the inflating portion.

Tests

The following tests were conducted on the endotracheal tubes of examples 6 to 9 and comparative example 2.

Test 3

The internal pressure of the cuff of each endotracheal tube was measured 180 minutes after the endotracheal tube was put in contact with laughing gas, and the rise in the internal pressure was calculated from the initial internal pressure of the cuff. The rise in the internal pressure of the cuff thus obtained was:

Example 6: 250 mmH$_2$O,
Example 7: 350 mmH$_2$O,
Example 8: 280 mmH$_2$O,
Example 9: 300 mmH$_2$O,
Comparative Example 2: 470 mmH$_2$O (after 30 min).

Test 4

The quality of the blow-molding, the withstanding pressure and the breaking strength of the cuffs of the endotracheal tubes of examples 6 to 8 were measured. The results were as shown in Table 4.

TABLE 4

| | Example 6 | Example 7 | Example 8 |
|---|---|---|---|
| Quality of blow-molding | o | o | o |
| Withstanding | 25 | 60 | 100 |

TABLE 4-continued

| | Example 6 | Example 7 | Example 8 |
|---|---|---|---|
| pressure (ml) Breaking strength (kgf) | 3.5 | 6.4 | 8.2 |

In Table 4, the withstanding pressure of the cuffs are represented by the amount of air injected until the cuffs break.

The first endotracheal tube of the present invention comprises a tubular body having a lumen and an inflation lumen provided in parallel with the lumen, and an inflatable and deflatable cuff attached to the distal end portion of the tubular body so as to surround the outside surface of the tubular body and communidate with the inflation lumen, and the cuff being made of a flexible fluoroplastic or a mixture of a flexible fluoroplastic and a thermoplastic resin. The first endotracheal tube of the present invention has the following advantages. The permeation of laughing gas into the cuff is substantially decreased, and hence damage to the trachea caused by the increase of the volume and the rise in the internal pressure of the cuff in use can be prevented. Further, the material for the cuff is blown-moldable, the cost of manufacture is reduced and the uniformity in the cuffs made is improved.

The second endotracheal tube of the present invention comprises a tubular body having a lumen and an inflation lumen provided in parallel with the lumen, and an inflatable and deflatable cuff attached to the distal end portion of the tubular body so as to surround the outside surface of the tubular body and communidate with the inflation lumen, and the cuff being made of a partly cross-linked resin with a low laughing gas permeability. The second endotracheal tube of the present invention has the following advantages. The permeation of laughing gas into the cuff is substantially decreased, and hence damage to the trachea caused by the increase of the volume and the rise in the internal pressure of the cuff in use can be prevented. Further, the material for the cuff is blown-moldable, the cost of manufacture is reduced and the uniformity in the cuffs made is improved. Further, the cuff has the sufficient physical properties (strength and withstanding pressure).

The manufacturing method of the present invention, comprising the processes of forming the tubular body, forming the cuff and attaching the cuff to the tubular body, and the process of forming the cuff comprising the process of forming a tube of a resin with a low laughing gas permeability, the process of irradiating the tube with electron beams or gamma rays to form cross-links partly in the resin, and the process of blow-molding the tube into the cuff, has the following advantages. Since the strength of a resin increases by irradiation, those which cannot be used because of the insufficient withstanding pressure and breaking strength of the cuff made of them in spite of their low laughing gas permeability become usable. Further, not completely cross-linked, the resin maintains the weldability to the tubular body.

We claim:

1. An endotracheal tube comprising a tubular body having a lumen and an inflation lumen provided in parallel with said lumen, and an inflatable and deflatable cuff attached to the distal end portion of the tubular body so as to surround the outside surface of the tubular body and communicate with said inflation lumen, and wherein said cuff is made of a flexible fluoroplastic in which the Shore A hardness is 90 or less and the gas permeability is 2 $cc(STP) \cdot cm/cm^2 \cdot sec - cmHg \times 10^{-10}$ or less or a mixture of a flexible fluoroplastic and a thermoplastic resin in which the Shore A hardness is 90 or less and the gas permeability is 2 $cc(STP) \cdot cm/cm^2 \cdot sec - cmHg \times 10 - 10$ or less.

2. An endotracheal tube in claim 1, in which said thermoplastic resin is at least one resin selected from the group consisting of polyurethane, polyamide, polyester, polypropylene, polyethylene, polyolefin elastomer, ethylene-vinyl acetate copolymer, polystyrene and polybutadiene.

3. An endotracheal tube in claim 1, wherein said flexible fluoroplastic is a graft copolymer of a fluororubber and a crystalline fluororesin wherein the fluororesin is grafted to the fluororubber or a block copolymer of fluororubber and crystalline fluororesin.

4. An endotracheal tube comprising a tubular body having a lumen and an inflation lumen provided in parallel with said lumen, and an inflatable and deflatable cuff attached to the distal end portion of the tubular body so as to surround the outside surface of the tubular body and communicate with said inflation lumen, characterized by said cuff being made of a partly cross-linked resin, having a gel fraction of 10 to 50%, with a low laughing gas permeability, and said resin is a flexible fluoroplastic and a thermoplastic resin and wherein said flexible fluoroplastic is a graft copolymer of a fluororubber and a crystalline fluororesin wherein the fluororesin is grafted to the fluororubber or a block copolymer of fluororubber and crystalline fluororesin.

5. An endotracheal tube in claim 4, in which the gel fraction of said partly cross-linked resin is 10 to 50%.

6. An endotracheal tube in claim 4, in which the Shore A hardness of said partly cross-linked resin is 90 or smaller.

7. An endotracheal tube comprising a tubular body having a lumen and an inflation lumen provided in parallel with said lumen, and an inflatable and deflatable cuff attached to the distal end portion of the tubular body so as to surround the outside surface or the tubular body and communicate with said inflation lumen, characterized by said cuff being made of a mixture of a flexible fluoroplastic and a thermoplastic resin, and the Shore A hardness of said mixture of a flexible fluoroplastic and a thermoplastic resin is 90 or smaller and wherein said flexible fluoroplastic is a graft copolymer of a fluororubber and a crystalline fluororesin wherein the fluororesin is grafted to the fluororubber or a block copolymer of fluororubber and crystalline fluororesin.

* * * * *